(12) United States Patent
Lardée

(10) Patent No.: US 10,159,647 B2
(45) Date of Patent: Dec. 25, 2018

(54) TABLET COMPRISING CROSPOVIDONE

(71) Applicant: DSM SINOCHEM PHARMACEUTICALS NETHERLANDS B.V., Delft (NL)

(72) Inventor: Abraham Cornelis Lardée, Echt (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 0 days.

(21) Appl. No.: 14/916,613

(22) PCT Filed: Sep. 18, 2014

(86) PCT No.: PCT/EP2014/069852
§ 371 (c)(1),
(2) Date: Mar. 4, 2016

(87) PCT Pub. No.: WO2015/040093
PCT Pub. Date: Mar. 26, 2015

(65) Prior Publication Data
US 2016/0193153 A1    Jul. 7, 2016

(30) Foreign Application Priority Data

Sep. 20, 2013  (EP) .................................. 13185368

(51) Int. Cl.
*A61K 9/20*  (2006.01)
*A61K 31/424*  (2006.01)
*A61K 31/43*  (2006.01)
*A61K 9/00*  (2006.01)

(52) U.S. Cl.
CPC .......... *A61K 9/2027* (2013.01); *A61K 9/0095* (2013.01); *A61K 9/2013* (2013.01); *A61K 9/2095* (2013.01); *A61K 31/424* (2013.01); *A61K 31/43* (2013.01)

(58) Field of Classification Search
CPC ........ A61K 31/424; A61K 31/43; A61K 9/20; A61K 9/2027; A61K 9/2095; A61K 9/2013
See application file for complete search history.

(56) References Cited

U.S. PATENT DOCUMENTS

2002/0006433 A1 *  1/2002  Davidson ............. A61K 9/0056
424/441
2002/0168405 A1  11/2002  Conley et al.
2003/0124187 A1 *  7/2003  Mention .............. A61K 9/2077
424/469

FOREIGN PATENT DOCUMENTS

EP        0 578 231      1/1994
WO       WO 98/35672    8/1998
WO       WO 00/66169    11/2000

OTHER PUBLICATIONS

Bruggink et al. Organic Process Research and Development, (1998), 2(2), p. 128-133.*
International Search Report for PCT/EP2014/069852, dated Nov. 5, 2014, 4 pages.
Written Opinion of the ISA for PCT/EP2014/069852, dated Nov. 5, 2014, 7 pages.
Brugging et al., "Penicillin acylase in the industrial production of beta-lactam antibiotics", Organic Process Research and Development, vol. 2, No. 2, Mar. 1, 1998, pp. 128-133.

* cited by examiner

*Primary Examiner* — Yong L Chu
(74) *Attorney, Agent, or Firm* — William D. Hare, Esq.; McNeely, Hare & War, LLP

(57) ABSTRACT

The present invention relates to a dispersible tablet comprising crospovidone, notably a tablet comprising crospovidone and a β-lactam antibiotic such as amoxicillin, to a method for preparing said tablet and to the use of said tablet.

20 Claims, 3 Drawing Sheets

TABLET COMPRISING CROSPOVIDONE

Figure 1:
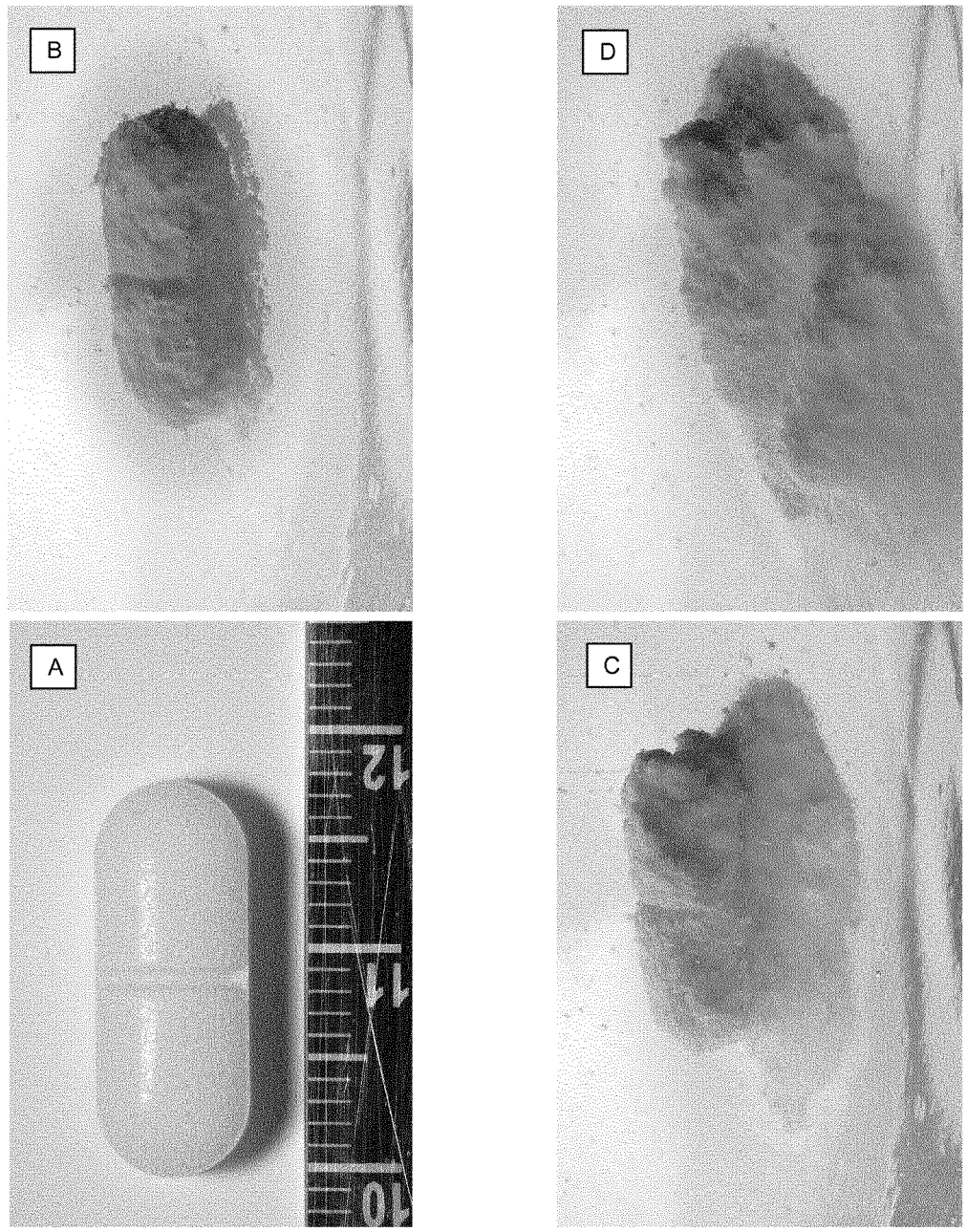

This application is the U.S. national phase of International Application No. PCT/EP2014/069852 filed 18 Sep. 2014, which designated the U.S. and claims priority to EP Patent Application No. 13185368.1 filed 20 Sep. 2013, the entire contents of each of which are hereby incorporated by reference.

FIELD OF THE INVENTION

The present invention relates to a dispersible tablet comprising crospovidone, notably a tablet comprising crospovidone and an antibiotic such as amoxicillin, to a method for preparing said tablet and to the use of said tablet.

BACKGROUND OF THE INVENTION

Crospovidone, also referred to as polyvinylpolypyrrolidone, PVPP, crospolividone or E1202, is a highly cross-linked modification of polyvinylpyrrolidone (PVP). Crospovidone is insoluble in water, though it still absorbs water and swells very rapidly generating a swelling force. This property makes it useful as a disintegrant leading to dispersible tablets. In addition, crospovidone can have advantageous properties such as absorption of certain compounds like endotoxins that may cause diarrhea. Crospovidone has E number code E1202 and is also used as a stabilizer.

The use of crospovidone as disintegrant in formulations comprising antibiotics is well known. In dispersible tablets, the amount of disintegrant normally present is from 5-10% (w/w), in some cases amounts as low as 2% (w/w) have been reported. This disintegrant may be crospovidone but can also be other disintegrants such as starch or combinations of crospovidone and other disintegrants. For example, GB 1403584 describes a dispersible tablet comprising close to 10% (w/w) of disintegrants, namely 8% (w/w) starch and less than 1% (w/w) crospovidone. WO 92/19227 describes a dispersible tablet comprising amoxicillin and clavulanic acid and from 2.73-3.78% (w/w) crospovidone. Other disclosures of dispersible tablets comprising an antibiotic and crospovidone are WO 91/07174 (18% crospovidone), CN 101524333 (15% crospovidone), ZA 9107789 (10% crospovidone), CN 101502511 (6% crospovidone), CN 1803135 (2-5% crospovidone) and EP 578231 (1.7% crospovidone) although exact disintegration times are not unambiguously disclosed in these documents making it difficult to judge whether indeed the disclosed tablets are dispersible in acceptable periods of time such as less than two or three minutes.

IN 185249B describes an improved process for preparation of rapidly soluble powders of beta-lactam antibiotics wherein a composition comprising amoxicillin trihydrate is disclosed comprising 0.2-0.8% (w/w) of crospovidone. However this concerns a powder, not a tablet suitable for rapid disintegration.

Presence of low amounts of crospovidone in tablets is also disclosed in WO 98/35672, however this document describes granulates, sachets, conventional non-dispersible tablets, chewable tablets but not dispersible tablets, although the same document also advocates that dispersible tablets will tend to comprise a relatively higher proportion of extra-granular disintegrant, to aid the dissolution process. Similarly, low amounts of crospovidone are disclosed in US 2002/168405 and WO 00/66169 but again these document concern chewable bilayer tablets and not dispersible tablets.

Finally, U.S. Pat. No. 5,262,171 discloses tablets comprising 0.5-10% of certain designed polyvinylpolypyrrolidones with specific K-values (K-30 to K-120), however the suitability of this type of disintegrant was only shown for active pharmaceutical ingredients other than antibiotics such as β-lactam antibiotics like amoxicillin, ampicillin, cephalexin, and the like. In particular, U.S. Pat. No. 5,262,171 discloses tablets comprising acetaminophen, acetylsalicylic acid, chloramphenicol, chlorpromazine, hydrochlorothiazide, methyl paraben, sulfathiazole and trimethoprim. Given the fact that these active pharmaceutical ingredients are different in chemical and physical behavior compared to the β-lactam antibiotics, the interaction with crospovidone cannot be extrapolated or predicted otherwise, in particular in view of the vast amount of prior art advocating the opposite.

In view of the fact that there is a continuous need for antibiotic tablets with as little as auxiliary components as absolutely needed, or as much as active pharmaceutical ingredient as possible, there remains a need for improved tablets comprising an antibiotic and less disintegrant compared to what is hitherto reported in the prior art.

DETAILED DESCRIPTION OF THE INVENTION

In the context of the present invention, the term 'disintegrant' refers to an agent used in the preparation of pharmaceutical tablets, which causes them to disintegrate and release their medicinal substances on contact with moisture. Disintegrants expand and dissolve when wet, causing the tablet to break apart in the digestive tract, releasing the active ingredients for absorption. Disintegrants ensure that when the tablet is in contact with water, it rapidly breaks down into smaller fragments, facilitating dissolution. Examples of disintegrants include alginates, cross-linked polymers such as crospovidone, cross-linked sodium carboxymethyl cellulose (croscarmellose sodium), formaldehyde-casein, starch, swell-able ion exchange resins and sodium starch glycolate.

In the context of the present invention, the term 'tablet' refers to a pharmaceutical dosage form comprising a mixture of active pharmaceutical ingredients and excipients, usually in powder form, pressed or compacted from a powder into a solid dose. The excipients can include diluents, binders or granulating agents, glidants (flow aids) and lubricants to ensure efficient tableting; disintegrants to promote tablet break-up in the digestive tract; sweeteners or flavors to enhance taste; and pigments to make the tablets visually attractive. A polymer coating is often applied to make the tablet smoother and easier to swallow, to control the release rate of the active ingredient, to make it more resistant to the environment (extending its shelf life), or to enhance the tablet's appearance. Tablets can be made in many shapes and colors to help distinguish different medicines. Tablets are often stamped with symbols, letters, and numbers, which enable them to be identified. The size of tablets to be swallowed may range from a few millimeters to about a centimeter. Some tablets are in the shape of capsules, and are also referred to as 'caplets'.

In the context of the present invention, the term 'dispersible tablet' refers to uncoated or film-coated tablets intended to be dispersed in water before administration giving a homogeneous dispersion as outlined in the WHO Revision of Monograph on Tablets (document QAS/09.324/Final, March 2011). Accordingly, dispersible tablets disintegrate within three minutes when examined by 5.3 Disintegration test for tablets and capsules as described in QAS/09.324/

Final, but using water R at 15-25°. The fineness of a dispersion according to QAS/09.324/Final is determined by placing 2 tablets in 100 mL of water R followed by stirring until completely dispersed. A smooth dispersion is produced, which passes through a sieve screen with a nominal mesh aperture of 710 μm. Preferably dispersible tablets disintegrate within 120 seconds when put in water, more preferably within 10 to 90 seconds, most preferably within 30 to 60 seconds after being placed in water. Dispersible tablets are more convenient for active pharmaceutical ingredients with insufficient stability in water. They are more easily transportable and they generate less handling and transportation costs for the same amount of active ingredient (less volume, less weight). Also dispersible tablets usually are easier to produce and the production costs are less, which makes them more affordable than standard liquid formulations. Other advantages include the use for very young children (0-6 months), ease of dispense (require minimal manipulation by health professionals and parents prior to use which minimizes the risk of errors), require a small amount of water for administration and can be dispersed in breast milk. As for liquid formulations, the taste of a dispersible tablet is a crucial parameter that will condition the acceptability, in particular by children, and the adherence to treatment. Taste masking may be obtained by adding flavours and/or sweeteners to the formulation. Dispersible tablets may be protected from the ambient humidity and may be packed in blisters (aluminium/aluminium) or bottles with a drying agent. Dispersible tablets may be dispersed in a small amount (5 to 10 ml) of liquid (clean water or milk) and the liquid may be softly stirred to aid dispersion before swallowing.

In a first aspect of the invention, there is disclosed a tablet comprising a β-lactam antibiotic and from 0.1 to 1.8% by weight of the tablet of a disintegrant, characterized in that said disintegrant comprises crospovidone. Preferably said β-lactam antibiotic is amoxicillin which preferably is in the form of amoxicillin trihydrate and the amount of amoxicillin trihydrate is from 50% to 97% by weight of the tablet, preferably from 60% to 96% by weight of the tablet, more preferably from 70% to 95% by weight of the tablet. Preferably, said amount of crospovidone is from 0.2 to 1.7% by weight of the tablet, more preferably from 0.3 to 1.6% by weight of the tablet, still more preferably from 0.4 to 1.5% by weight of the tablet, still more preferably from 0.5 to 1.4% by weight of the tablet. Most preferably the amount of crospovidone is 1.0±0.3% by weight of the tablet, still most preferably 0.9±0.1% by weight of the tablet and still most preferably 0.8±0.15% by weight of the tablet.

Traditionally, amoxicillin is prepared from penicillin G or penicillin V following complex chemical conversions involving the intermediate formation of 6-amino penicillanic acid, see for example J. Verweij et al. (*Recl. Trav. Chim. Pays-Bas* (1993) 112, 66-81 and references cited therein). There are various drawbacks associated with this approach, the main ones being the fact that such processes require hazardous and environmentally harmful chemicals. Such chemicals, mostly solvents such as butyl acetate, dichloromethane, dimethyl acetamide, isopropanol and/or pyridine and auxiliary chemicals such as pivalic acid and triethyl amine, end up as unwanted contaminants in the final product. Levels of residual solvents and auxiliary chemicals in amoxicillin are often significant and values for individual contaminants ranging from 300 to 2000 ppm are not unusual. A well-known contaminant such as dichloromethane may often occur in ranges of from 1000 to 5000 ppm.

Fortunately, in the last two decades major improvements have been realized with the introduction of environmentally benign enzyme-catalyzed processes that are carried out in water such as described in A. Bruggink et al. (*Org. Proc. Res. Dev.* (1998) 2, 128-133 and references cited therein). Consequently, the majority of β-lactam antibiotics nowadays rarely contain organic solvents or hazardous auxiliary chemicals other than perhaps minute traces (less than 300 ppm) of harmless low-carbon alcohols such as ethanol or methanol. The foregoing is certainly also true for amoxicillin. Typically, amoxicillin trihydrate prepared by enzymatic synthesis and used for the tablets of the present invention contains less than 500 ppm of a compound chosen from the list consisting of dichloromethane, isopropanol, pivalic acid and triethyl amine.

Thus, in one embodiment said amoxicillin trihydrate is prepared by enzyme catalyzed condensation of 6-aminopenicillanic acid and an ester or amide of 4-hydroxyphenyl glycine. It was surprisingly found that the application of amoxicillin trihydrate thus obtained leads to tablets with good disintegrating properties at hitherto unprecedented low amounts of disintegrants.

In another embodiment, the tablet according to the present invention may comprise an additional pharmaceutical active ingredient. This may be another antibiotic such as ampicillin, cefaclor, cefadroxil, cephalexin or cephradine but may also be a β-lactamase inhibitor such as clavulanic acid, sulbactam or tazobactam or salts thereof. A preferred additional pharmaceutical active ingredient is clavulanic acid or a pharmaceutically acceptable salt thereof.

In another embodiment, the tablet of the present invention may comprise an artificial flavor such as banana, kiwi, mango, orange, raspberry, strawberry and the like or combinations thereof. Artificial flavors usually have a positive effect on ease of administration, particularly in pediatric applications. The tablet of the present invention may be coated or non-coated. When the tablet of the present invention is coated, artificial flavors may be incorporated in the coating layer.

One of the most surprising advantages of the tablet of the present invention are the unprecedented low disintegration times of less than 15 min, preferably less than 10 min, more preferably less than 5 min and even less than 1 min at the low crospovidone concentrations mentioned above.

In a second aspect of the invention there is disclosed a method for the preparation of the tablet of the first aspect of the invention comprising sifting a β-lactam antibiotic such as amoxicillin, crospovidone and an optional first group of additives followed by mixing and addition of a lubricant followed by tableting. Thus, the second aspect of the invention provides a method for the preparation of a tablet comprising the steps of:

(a) Sifting a β-lactam antibiotic, crospovidone and an optional first group of additives
(b) Mixing the components obtained in step (a);
(c) Adding a lubricant to the mixture obtained in step (b);
(d) Compressing the mixture obtained in step (c) into a tablet,
wherein the amount of crospovidone is from 0.1-1.8% by weight of said tablet.

The β-lactam antibiotic may be any semi synthetic penicillin such as amoxicillin or ampicillin or any semi synthetic cephalosporin such as cefaclor, cefadroxil, cefprozil, cephalexin, cephradine or even combinations thereof. As outlined in the first aspect of the invention, the β-lactam antibiotic preferably is prepared according to known enzymatic procedures in aqueous environment and preferably is amoxicillin trihydrate.

In the tableting process, the appropriate amount of active ingredient must be brought in each tablet. In a preferred embodiment, all ingredients are therefore well mixed prior to tableting. Preferably, in order to obtain a sufficiently homogenous mix of the components assuring an even distribution of the active compound in the final tablet, granulation prior to compression to applied. For the person skilled in the art, two basic techniques are available to granulate powders for compression into a tablet: wet granulation and dry granulation. Powders that can be mixed well do not require granulation and can be compressed into tablets through direct compression.

In wet granulation, a liquid binder is used to lightly agglomerate the powder mixture. The amount of liquid has to be properly controlled, as over- or under-wetting will cause the granules to be too soft or too hard. Aqueous solutions have the advantage of being safer to deal with than solvent-based systems. Low shear wet granulation processes use very simple mixing equipment, and can take a considerable time to achieve a uniformly mixed state. High shear wet granulation processes use equipment that mixes the powder and liquid at a very fast rate, and thus speeds up the manufacturing process. Fluid bed granulation is a multiple-step wet granulation process performed in the same vessel to pre-heat, granulate, and dry the powders. It may be used advantageously as it allows close control of the granulation process.

In dry granulation, granules are created by compacting the powder blend under low pressure. The compacts so-formed are broken up gently to produce granules (agglomerates). This process is advantageously used when the product to be granulated is sensitive to moisture and heat. Dry granulation can be conducted on a tablet press using slugging tooling or on a roll press called a roller compactor. Dry granulation equipment offers a wide range of pressures to attain proper densification and granule formation. Dry granulation has the advantage of being simpler than wet granulation. Dry granulation requires drugs or excipients with cohesive properties and in one embodiment a dry binder may need to be added to the formulation to facilitate the formation of granules. Surprisingly, a dispersible tablet can be obtained by dry mixing of the active pharmaceutical ingredient with very low amounts of a disintegrant and remaining functional excipients.

In another embodiment, following granulation, a lubrication step may be used. This can prevent unwanted sticking of the tableting blend to the equipment during the tableting process. This usually involves low shear blending of the granules with a powdered lubricant. Suitable lubricants are magnesium stearate or stearic acid.

In one embodiment, the process of the second aspect of the invention comprises mixing a β-lactam antibiotic and optionally a β-lactamase inhibitor in the appropriate amounts and subsequently mixed with the other excipients excluding the lubricant. Mixing may be done in a standard way known in the field such as by means of tumbler mixing or (high) shear mixing. When mixing is done, the final amount of lubricant such as magnesium stearate is added. This is preferably done in the second stage to make sure the magnesium stearate, or any alternate stearic acid derivative, is working properly as a glidant during tableting. The resulting mixture may be fed into a tablet press like the Fette RoTab T, M or MinTab T machine supplied by Kg-Pharma. In one embodiment the tablets are made using a multi tip tool. A multiple tip tool is a punch body that houses more than one tip per punch therefore allowing for the production of more than one tablet per station on the press turret. This means that it is possible to produce several times the output of a press running with standard single tip punches. Each punch is fitted with the required amount of tips. The tip number changes with the size of the tablets. For example, a 2 mm tip of category B has 16 tips per punch, the D-type tool has 35 tips. These punches are supplied by many companies. Suitable examples are the Fette punches, like Fette 441. The powder is tableted to the required strength, which may be set in the tablet press and measured afterwards. Suitable equipment for testing may be a DIYTrade YD-1 Tablet hardness tester, A ERWEKA TBH-28 hardness tester or a Casburt C53 Tablet hardness tester. Also the friability may be measured, for example using a Key International Inc Ft-400 Friability tester or an ERWEKA TA-UZ friability tester.

Disintegration of the tablet may be tested according to the European and Japanese Pharmacopoeia. The apparatus consist of a basket-rack assembly which is immersed in a temperature controlled liquid, in this case tap water. The basket is raised and lowered in the liquid at a constant frequency between 29 and 32 cycles per minute over a distance between 53 and 57 mm. The volume of the fluid in the vessel is such that at the highest point of the upward stroke the wired mesh of the basket remains at least 15 mm below the surface of the liquid and descends to not more than 25 mm from the bottom of the vessel on the downward stroke. In the basket a rack is present consisting of six open ended tubes in which the tablets are placed when measuring the disintegration rates. The mesh should be such that the tablets cannot fall out of the tube bottom during the movement of the device. The disintegration may be measured using tap water of 37±2° C. The time to full disintegration is monitored by recording the moment that the tablet has fully disappeared from the tube. The insoluble parts of the formulation will fall through the mesh below the tube in which the tablets were placed.

Regardless of the process used for the preparation of the tableting blend, the process of making a tablet by powder compaction may, in summary, be performed as follows. First, the powder is filled into a container such as a die form. The mass of powder is determined by the position of the lower punch in the die, the cross-sectional area of the die, and the powder density. At this stage, adjustments to the tablet weight are normally made by repositioning the lower punch. Following filling of the die, the upper punch is lowered into the die and the powder is compressed, preferably uni-axially, to a porosity of between 5 and 20%. The compression may take place in multiple stages (main compression and sometimes pre-compression or tamping). Finally, the upper punch is pulled up and out of the die (decompression), and the tablet is ejected from the die by lifting the lower punch until its upper surface is flush with the top face of the die. This process is repeated for each tablet.

In a third aspect of the invention there is disclosed the tablet of the first aspect of the invention for use in the treatment of bacterial infections. For example, tablets comprising amoxicillin may be used in the treatment of a number of infections, including acute otitis media, Streptococcal pharyngitis, pneumonia, skin infections, urinary-tract infections, *Salmonella*, lyme disease, and chlamydia infections. Tablets comprising amoxicillin may also be used to prevent bacterial endocarditis in high-risk people following dental treatment with the objective to prevent *Streptococcus pneumoniae* and other encapsulated bacterial infections in those without spleens, such as people with sickle-cell disease, and for both the prevention and the treatment of anthrax. Amoxicillin and amoxicillin-clavulanate are recommended by guidelines as the first-choice drug for bacterial sinusitis. Tablets comprising amoxicillin may be used for the treatment of skin infections, such as acne vulgaris.

In a fourth aspect of the invention there is disclosed a package comprising the tablet of the first aspect of the invention. Suitable packages are so-called blister packages. When the tablets are so-called mini tablets they may also be packaged is sachets. Sachets comprising a multitude of mini tablets are useful for application of the tablets on or in a food stuff, which facilitates pediatric application.

In a fifth aspect of the invention there is disclosed the use of crospovidone in preparing a dispersible tablet comprising a β-lactam antibiotic wherein the amount of crospovidone is from 0.1-1.8% by weight of said dispersible tablet.

LEGEND TO THE FIGURES

FIG. 1 represents the dissolution of a 500 mg amoxicillin tablet in Dutch tap water. The tablet comprises amoxicillin trihydrate (574 mg), aspartame (10 mg), crospovidone (6.0 mg), magnesium stearate (4.7 mg), microcrystalline cellulose (80 mg) and strawberry flavor (6.3 mg). Panel A: Tablet prior to contacting with water along a ruler with main numbered dividing lines in cm; Panel B: Tablet, 10 seconds after submerging in water; Panel C: Tablet, 30 seconds after submerging in water; Panel D: Tablet, 60 seconds after submerging in water.

Figure 2:
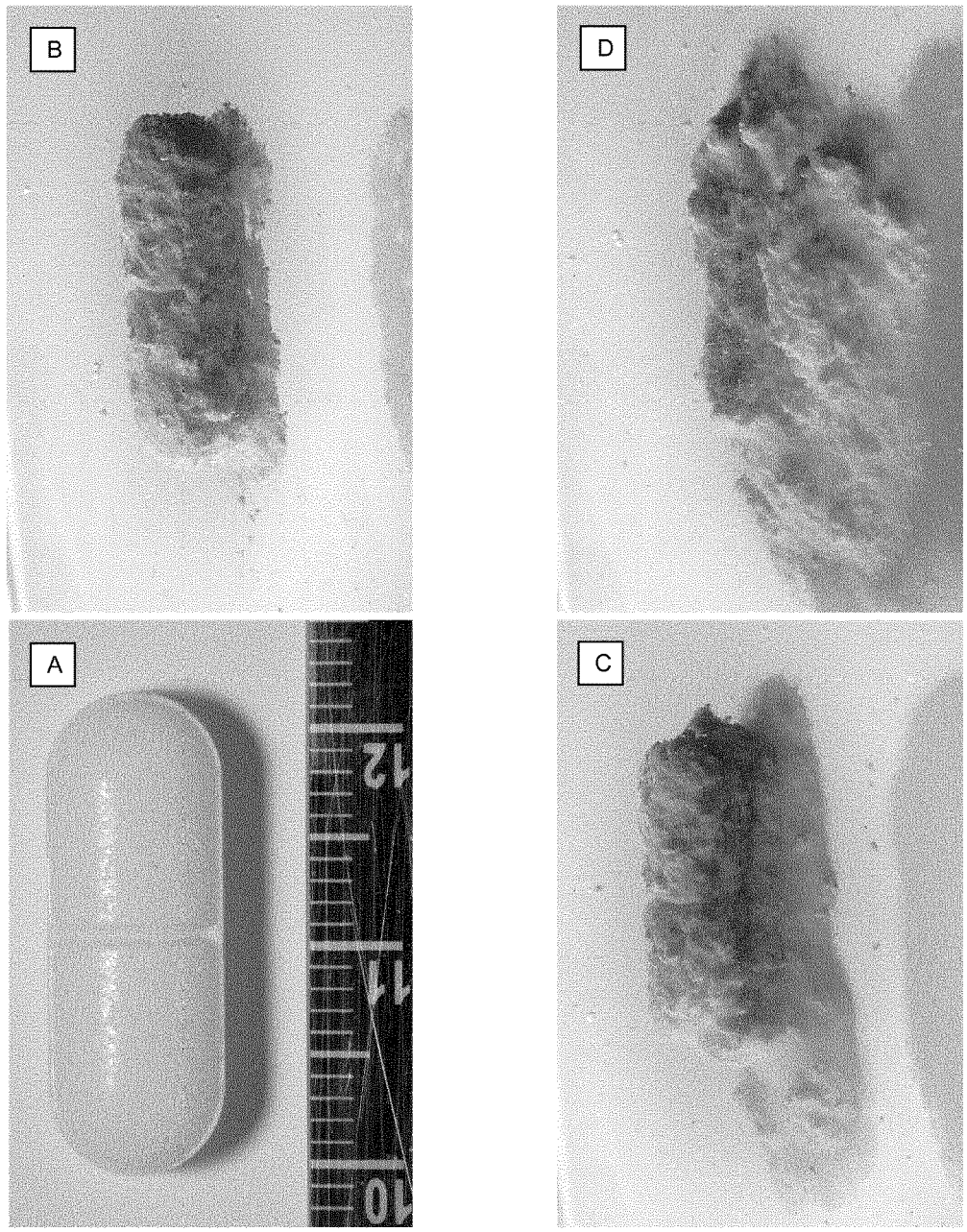

FIG. 2 represents the dissolution of a 750 mg amoxicillin tablet in Dutch tap water. The tablet comprises amoxicillin trihydrate (861 mg), aspartame (15 mg), crospovidone (9.0 mg), magnesium stearate (7.0 mg), microcrystalline cellulose (121 mg) and strawberry flavor (9.4 mg). Panels A-D as outlined above for FIG. 1.

Figure 3:
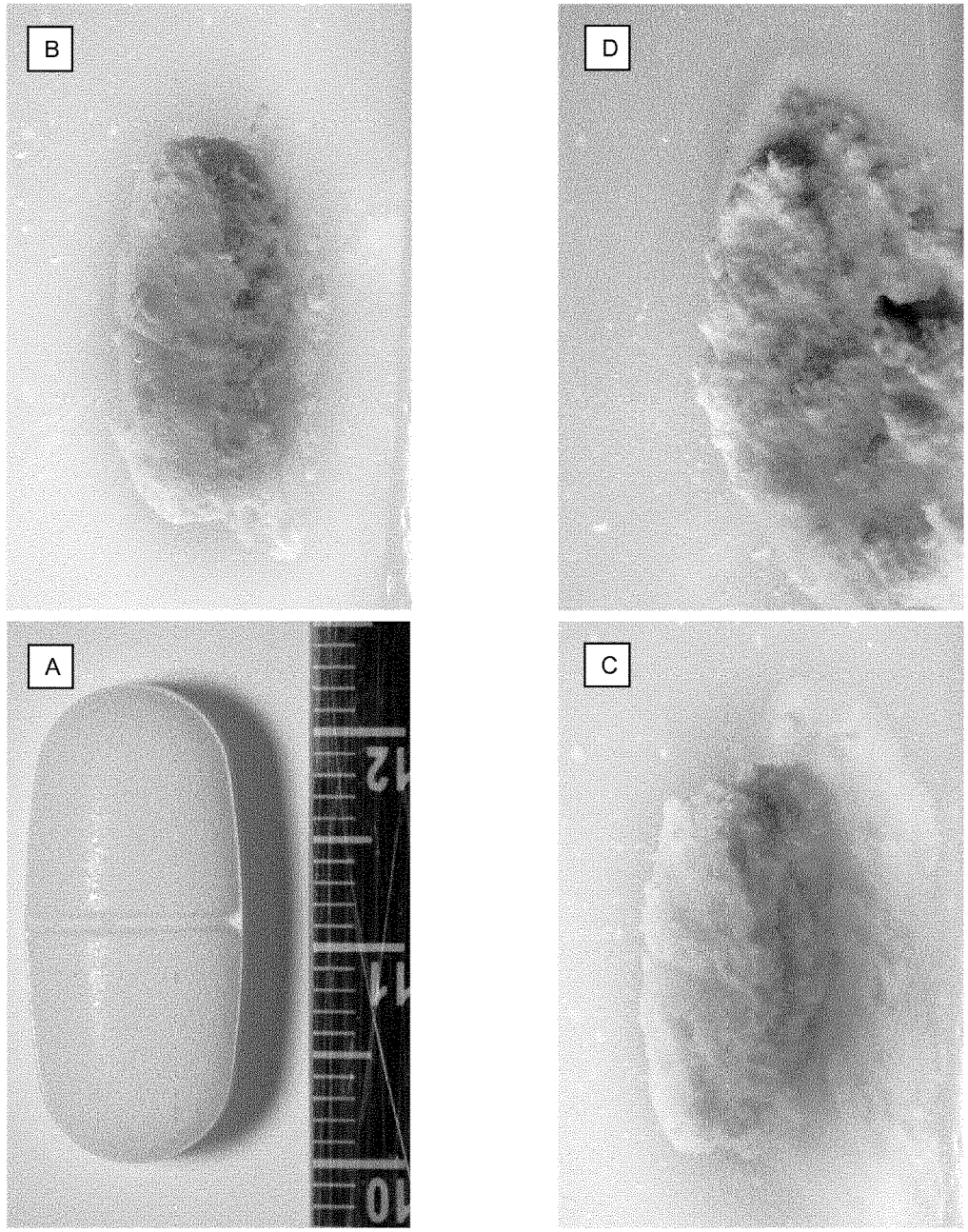

FIG. 3 represents the dissolution of a 1000 mg amoxicillin tablet in Dutch tap water. The tablet comprises amoxicillin trihydrate (1148 mg), aspartame (20 mg), crospovidone (12 mg), magnesium stearate (9.4 mg), microcrystalline cellulose (161 mg) and strawberry flavor (13 mg). Panels A-D as outlined above for FIG. 1.

EXAMPLES

Example 1

Preparation of 500 mg, 750 mg and 1000 mg Amoxicillin Tablets

At 25° C. and a relative humidity of 55%, amoxicillin trihydrate, crospovidone, aspartame, microcrystalline cellulose, strawberry flavor and magnesium stearate were weighed in suitable amounts in separate containers. The amoxicillin trihydrate was sifted through an ASTM #30 (600 μm) screen and the remains were milled with an oscillating granulator using a 430 μm screen. The sifted and milled amoxicillin trihydrate fractions were mixed in a blender for 5 min. The required quantity of amoxicillin trihydrate was and transferred into a blender, together with the appropriate amount (see Table 1) of crospovidone, aspartame, microcrystalline cellulose and strawberry flavor, sifted through an ASTM #30 (600 μm) screen.

TABLE 1

Unit composition of amoxicillin tablets

| Ingredient | Functional category | Amount per tablet (mg) | | | Amount per tablet (% w/w) |
|---|---|---|---|---|---|
| | | 500 mg tablet | 750 mg tablet | 1000 mmg tablet | |
| Amoxicillin trihydrate | Active Pharmaceutical Ingredient | 574.00 | 861.00 | 1148.00 | 84.25 |
| Crospovidone | Disintegrant | 6.02 | 9.02 | 12.03 | 0.88 |
| Cellulose, microcrystalline | Diluent | 80.39 | 120.58 | 160.77 | 11.80 |
| Aspartame | Sweetener | 10.00 | 15.00 | 20.00 | 1.47 |
| Strawberry flavor | Flavoring agent | 6.25 | 9.38 | 12.50 | 0.92 |
| Magnesium stearate | Lubricant | 4.69 | 7.03 | 9.37 | 0.69 |
| Total core tablet | | 681.35 | 1022.01 | 1362.67 | 100.00 |

The mixture was mixed in the blender for 10 min. Magnesium stearate was sifted through an ASTM #60 (250 μm) screen and transferred to the blender after which mixing was continued for another 5 min. The resulting lubricated blend was compressed with the parameters and results as outlined in Table 2.

TABLE 2

| | In-process parameters | | |
|---|---|---|---|
| Strength | 500 mg tablet | 750 mg tablet | 1000 mg tablet |
| In-process parameters for amoxicillin dispersible tablets and amoxicillin tablets | | | |
| Appearance | White to off-white, capsule shaped tablets | White to off-white, modified capsule shaped tablets | White to off-white, caplet shaped tablets |
| Average weight (mg) | 681.35 ± 2% | 1022.01 ± 2% | 1362.67 ± 2% |
| Hardness (Kp) | 11-17 | 13-19 | 13-19 |
| Thickness (mm) | 5.2 ± 0.2% | 7.2 ± 0.2% | 7.4 ± 0.2% |
| Friability (% w/w) | 1.0 | 1.0 | 1.0 |
| Additional in-process parameters for amoxicillin dispersible tablets | | | |
| Disintegration time at 15-25° C. (min) (see also Example 2) | <3 | <3 | <3 |

TABLE 2-continued

| In-process parameters | | | |
|---|---|---|---|
| Strength | 500 mg tablet | 750 mg tablet | 1000 mg tablet |
| Additional in-process parameters for amoxicillin tablets | | | |
| Disintegration time at 15-25° C. (min) | 15 | 15 | 15 |

Example 2

Disintegration of Amoxicillin Tablets in Water

The 500 mg, 750 mg and 1000 mg amoxicillin-comprising tablets of Example 1 (Table 1) were submerged in water and the disintegration was observed as a function of time. The results are as outlined in Table 3. From this Table it was concluded that disintegration for all three tablets occurred fast and was complete within one minute.

TABLE 3

Disintegration of amoxicillin tablets in water (+ = Surface disintegration; ++ = Substantial disintegration; +++ = Substantial disintegration with significant cavities in tablet; ++++ = Complete disintegration)

| Time (seconds) | 500 mg tablet | 750 mg tablet | 1000 mg tablet |
|---|---|---|---|
| 10 | + | + | + |
| 30 | +++ | +++ | ++ |
| 60 | ++++ | ++++ | ++++ |

The invention claimed is:

1. A noncoated dispersible tablet comprising a β-lactam antibiotic, from 0.65-1.6% by weight of the tablet of a disintegrant, characterized in that said disintegrant comprises crospovidone which is present in an amount of 0.80±0.15% by weight of the tablet, and one or more pharmaceutically acceptable excipients, wherein the β-lactam antibiotic, the disintegrant and the pharmaceutically acceptable excipients in the tablet are in the form of a mixture.

2. The tablet according to claim 1, wherein the β-lactam antibiotic is amoxicillin trihydrate.

3. The tablet according to claim 2, wherein the amoxicillin trihydrate is present in an amount of from 50% to 97% by weight of the tablet.

4. The tablet according to claim 1, wherein the tablet comprises less than 500 ppm of a compound selected from the group consisting of dichloromethane, isopropanol, pivalic acid and triethyl amine.

5. The tablet according to claim 1, wherein the tablet further comprises an additive.

6. The tablet according to claim 5, wherein the additive comprises at least one of a β-lactamase inhibitor and an artificial flavor.

7. The tablet according to claim 6, wherein the β-lactamase inhibitor is clavulanic acid or a pharmaceutically acceptable salt thereof.

8. The tablet according to claim 1, wherein the tablet disintegrates within from 30 to 120 seconds after being placed in water in accordance with section 5.3 of Document QAS/09.324/Final dated March 2011 of the WHO Revision of Monograph on Tablets using water at a temperature of 15-25° C.

9. (Rejoined and Previously Amended) A method for the preparation of a dispersible tablet according to claim 1 comprising the steps of:
 (a) sifting tablet components comprising the β-lactam antibiotic, the disintegrant in an amount from 0.65-1.6% by weight of the tablet, the disintegrant comprising crospovidone which is present in an amount of 0.80±0.15% by weight of the tablet, and an optional first group of additives;
 (b) mixing the components obtained in step (a) to obtain a mixture thereof;
 (c) adding a lubricant to the mixture obtained in step (b); and
 (d) compressing the mixture obtained in step (c) into a tablet, wherein the amount of crospovidone is from 0.1-1.6% by weight of said tablet.

10. The method according to claim 9, wherein the β-lactam antibiotic is amoxicillin trihydrate.

11. The method according to claim 9, wherein said lubricant is magnesium stearate.

12. A package comprising the tablet according to claim 1.

13. A noncoated dispersible tablet comprising a β-lactam antibiotic and from 0.65-1.6% by weight of the tablet of a disintegrant which comprises crospovidone, the crospovidone being present in an amount of 0.80±0.15% by weight of the tablet, microcrystalline cellulose, a lubricant and one or more of a flavor and sweetener, wherein the β-lactam antibiotic, disintegrant, microcrystalline cellulose, lubricant and flavor and/or sweetener are in the form of a mixture, and wherein the tablet disintegrates within from 30 to 120 seconds after being placed in water in according with section 5.3 of Document AAS/09.324/Final dated March 2011 of the WHO Revision of Monograph on Tablets using water at a temperature of 15-25° C.

14. The tablet according to claim 13, wherein the β-lactam antibiotic is amoxicillin trihydrate.

15. The tablet according to claim 14, wherein the amoxicillin trihydrate is present in an amount of from 50% to 97% by weight of the tablet.

16. The tablet according to claim 13, wherein the tablet comprises less than 500 ppm of a compound selected from the group consisting of dichloromethane, isopropanol, pivalic acid and triethyl amine.

17. The tablet according to claim 13, wherein the tablet further comprises an additive.

18. The tablet according to claim 17, wherein the additive comprises at least one of a β-lactamase inhibitor and an artificial flavor.

19. The tablet according to claim 18, wherein the β-lactamase inhibitor is clavulanic acid or a pharmaceutically acceptable salt thereof.

20. A package which comprises the tablet according to claim 13.

* * * * *